United States Patent [19]

Kenny

[11] 4,344,193
[45] Aug. 17, 1982

[54] MENISCUS PROSTHESIS

[76] Inventor: Charles H. Kenny, 276 South St., Pittsfield, Mass. 01201

[21] Appl. No.: 211,292

[22] Filed: Nov. 28, 1980

[51] Int. Cl.$^3$ .............................................. A61F 1/24
[52] U.S. Cl. ................................. 3/1.911; 128/92 C; 128/DIG. 21
[58] Field of Search ................................ 3/1.9–1.911; 128/92 C, DIG. 21

[56] References Cited

U.S. PATENT DOCUMENTS

| Re. 29,757 | 9/1978 | Helfet | 3/1.911 |
| 3,798,679 | 3/1974 | Ewald | 3/1.911 |
| 3,816,855 | 6/1974 | Saleh | 3/1.911 |
| 3,869,731 | 3/1975 | Waugh et al. | 3/1.911 |
| 3,879,767 | 4/1975 | Stubstad | 3/1.91 |
| 3,924,277 | 12/1975 | Freeman et al. | 3/1.911 |
| 3,927,423 | 12/1975 | Swanson | 3/1.91 |
| 4,052,753 | 10/1977 | Dedo | 3/1 |
| 4,081,866 | 4/1978 | Upshaw et al. | 3/1.911 |
| 4,085,466 | 4/1978 | Goodfellow et al. | 3/1.911 X |
| 4,178,641 | 12/1979 | Grundei et al. | 3/1.911 |
| 4,207,627 | 6/1980 | Cloutier | 367/142 |

OTHER PUBLICATIONS

Minns et al, "The Mechanical Testing . . . Prosthesis"; *Clinical Orthopaedics and Related Research*, Dec. 1978, pp. 268–275.
Howmedica, Inc., brochure F-16, "MacIntosh Tibial Plateaus".
*Hospital Tribune*, Payer Article, "New Artifical Knee is Said to Offer Smoother Locomotion", Nov. 1980, pp. 3 and 16.

*Primary Examiner*—Ronald L. Frinks
*Attorney, Agent, or Firm*—Cushman, Darby & Cushman

[57] ABSTRACT

A meniscus prosthetic device for a human knee joint can be inserted into the knee joint so that the articulating cartilage in the knee totally remains intact. The prosthesis device translates between the articulating cartilage during normal knee movement. Insertion of the prosthetic device is accomplished by applying force on the ends of the device, thereby elastically spreading them, and placing the device between the tibial articulating cartilage and one of the femoral condyles. The forces thus applied can then be released causing the device to conform to its original C-shape. Prominences on the ends of the device may superiorly extended into the space defined by the femoral condyles, thereby securing the device in place.

17 Claims, 8 Drawing Figures

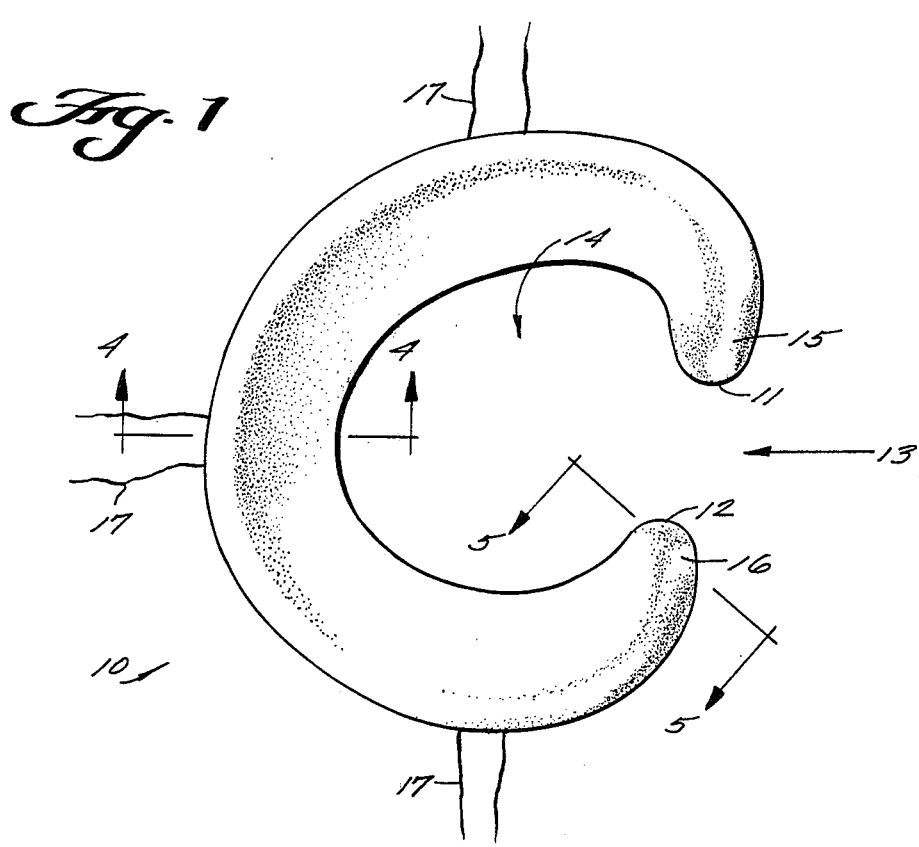
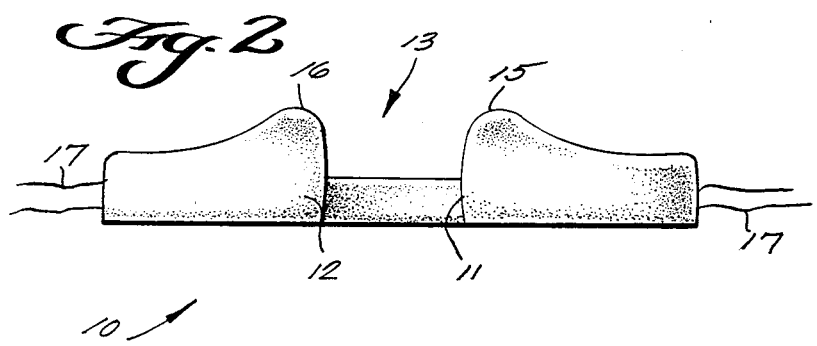
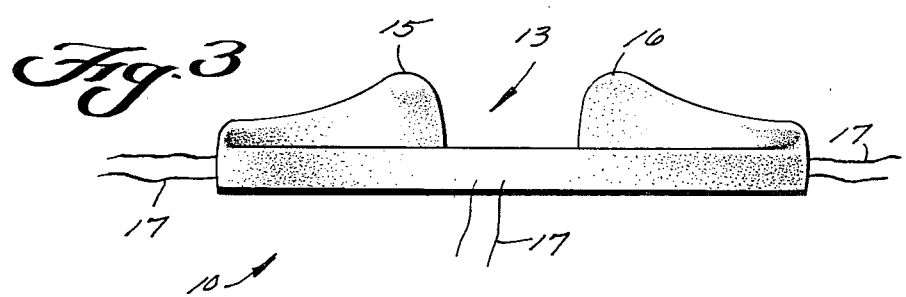

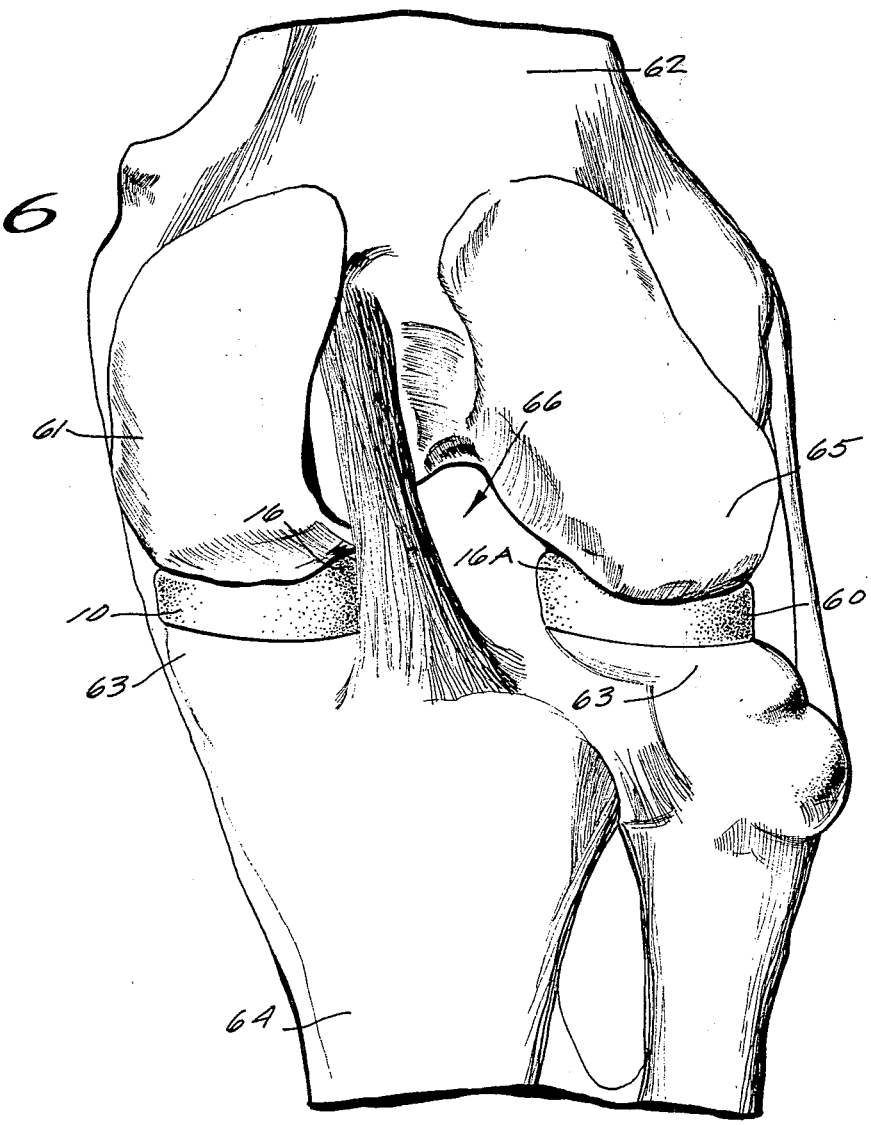

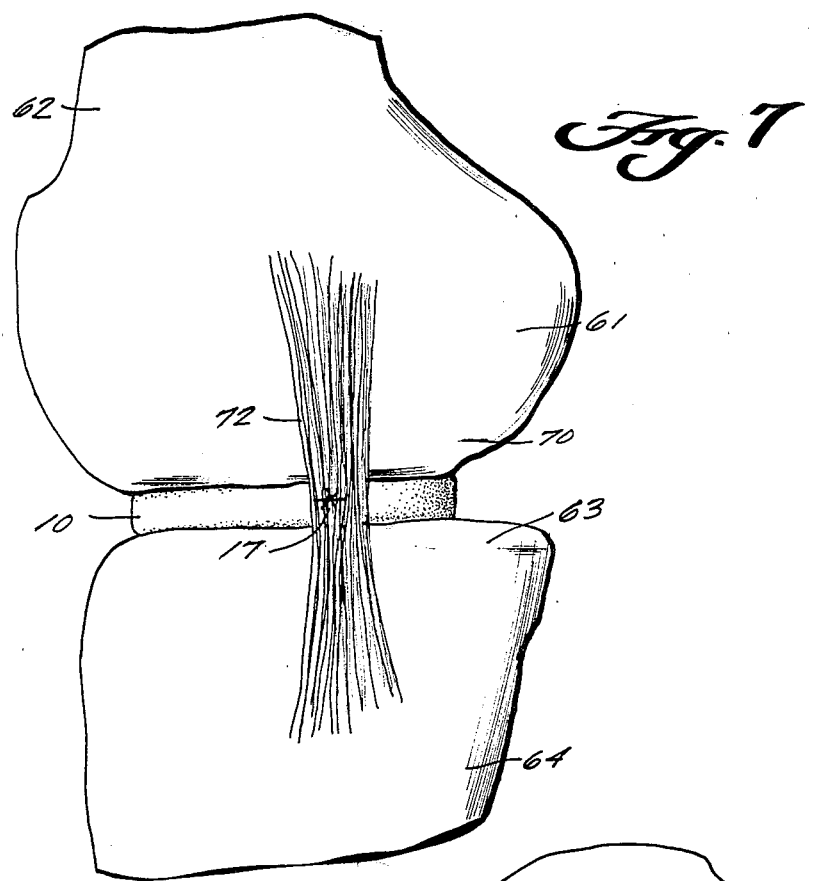
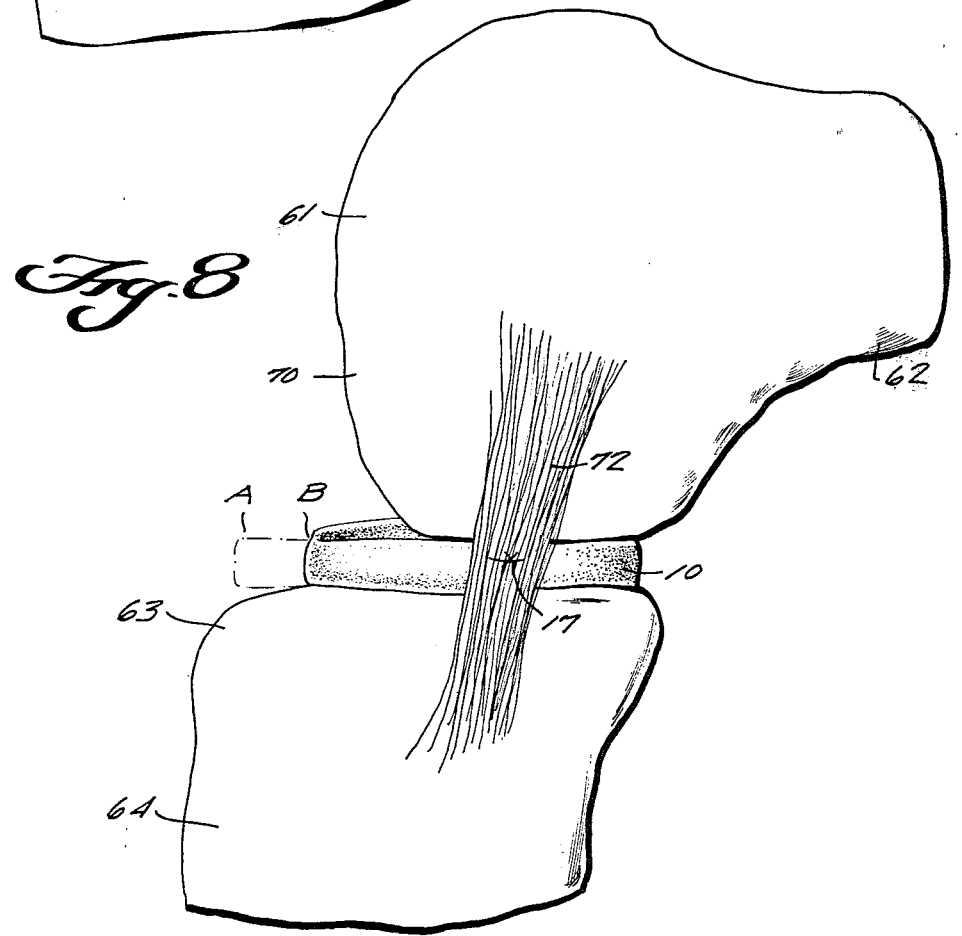

MENISCUS PROSTHESIS

BACKGROUND AND SUMMARY OF THE INVENTION

In recent years, medical science and biological engineers have been developing prosthetic devices to replace natural components of the human body. The prosthetic devices have as their primary objective the replacement of natural bodily components which may have become diseased or damaged while at the same time preserving the natural bodily function associated with the replaced organ, limb or other body component. The prosthetic replacement of natural body components should not be confused, however, with the natural transplantation of a similar living organ, limb or other body component. Prosthetic devices are totally man-made, being constructed primarily of synthetic materials while transplantation is concerned with the replacement of a natural body organ or component received from a human donor.

The prosthetic devices constructed primarily from such synthetic materials must, of course, be compatible with living human tissue and, additionally, must be capable of performing the bodily function of the removed natural component. A successful prosthetic device will last for an indefinite period of time without noticeable degeneration due to the inherent properties of the synthetic materials utilized. The present invention relates to a type of prosthetic device utilized in a human knee. The knee is a bicondylar joint formed by the articulation between the condyles of the femur and the articular cartilage of the tibia.

Typical conventional prosthetic devices for the knee are shown in U.S. Pat. Nos. 3,924,277, 4,081,866, 4,207,627, RE. 29,757, and 3,869,731 (the disclosures of which are herein incorporated by reference herein). The major problem associated with the conventional knee joint prosthetic devices is the necessity of surgically removing or altering the articulating cartilage of both the femur and tibia. Additionally, many conventional prosthetic devices require that the device be fixedly secured to the femur and tibia by means of surgical cement or the like. The necessity for removing or altering the femoral and tibial cartilage prior to the implantation of the conventional prosthetic devices increases the cost of surgical services associated with such implantation.

According to the present invention, however, a prosthetic device for a human knee is provided such that the articulating cartilage of the femur and tibia remains totally intact. Additionally, the prosthetic device according to the present invention is not intended to be surgically cemented in place. The device is designed to provide a natural substitute for damaged or diseased components in the knee joint area, such as, for example, arthritic conditions, damage due to automobile or athletic injuries, and the like. The device according to the present invention can be easily manufactured, and more efficiently inserted into the human knee, so that manufacturing costs and the cost of surgical services are reduced compared to the conventional prosthetic devices.

The prosthetic device according to the present invention may be manufactured in varying sizes conforming to the varying sizes of the human body and, in addition, the inherent varying size of the inner and outer condyle of the femur.

Therefore, it is a primary object of the present invention to provide a prosthetic device which may be easily manufactured and quickly positioned by surgical methods, without requiring the surgical removal or alteration of the femur and tibial articulating surfaces. This and other objects of the invention will become clear from an inspection of the detailed description of the invention, and from the appended claims.

BRIEF DESCRIPTION OF THE DRAWINGS

FIG. 1 is a top view of a representative medial meniscus prosthetic device for a human right knee;

FIG. 2 is a lateral view of the device of FIG. 1;

FIG. 3 is a medial view of the device of FIG. 1;

FIGS. 4 and 5 are cross-sectional views taken along lines 4—4 and 5—5, respectively, of FIG. 1;

FIG. 6 is a posterior view of a human right knee in extension showing the device of FIG. 1 and a corresponding lateral device in position;

FIG. 7 is a medial view of a human right knee in extension showing the representative medial device of FIG. 1 in position; and FIG. 8 is a medial view of a human right knee in flexion showing the translational movement of the representative medial device of FIG. 1.

DETAILED DESCRIPTION OF THE INVENTION

The representative embodiment of the present invention is illustrated generally in FIG. 1 wherein the prosthetic device for a human knee is shown as a medial device for placement in a human right knee. It should be understood that the symmetry of the human body allows for the general representative device depicted in FIG. 1 to be capable of performing its intended function in both the medial and lateral positions of a human right knee, with the devices for the left knee being generally a mirror image of the right knee devices. While the basic embodiment of the present invention remains unchanged, the varying sizes of the human knee coupled with the inherent varying size of the inner and outer condyles requires that these variables be taken into account when sizing a device of the present invention for placement in a human knee. Therefore, while only the medial meniscus prosthetic device for a human right knee is depicted in the drawings, it should be understood that the lateral meniscus device for the human right knee is generally a mirror image thereof, while the medial and lateral meniscus devices for a human left knee are generally mirror images of the respective devices for a human right knee.

Referring more specifically to FIG. 1, it is seen that the representative medial meniscus prosthetic device 10 generally is a C-shaped structure having the terminal ends 11, 12 in close proximity to one another and defining a space 13 therebetween. The generally circular structure of the device additionally defines an inner space 14 with which a femoral condyle interacts. The device in its preferred embodiment has two raised prominences 15, 16 on each of the terminal ends of the prosthetic device. The prominences 15, 16 can be seen more clearly in FIG. 2 viewing the meniscus prosthetic device 10 from the lateral side wherein the prominences 15, 16 are noticeably raised above the general surface of the device 10.

The prominences 15, 16, when properly placed in a human knee superiorly enter the space formed by the femoral condyles and thus secure the prosthetic device in position. Additionally, the prominences 15, 16 also encourage translational movement of the device over the articulating surfaces when properly positioned in the knee. Sutures 17 can be seen in FIG. 1 at the anterior, posterior and medial positions of the prosthetic device 10. As stated above, the prominences 15, 16 can sufficiently hold the meniscus prosthetic device 10 in proper position. However, a physician in his judgment, may wish to utilize the optional sutures 17 to further secure the meniscus prosthetic device 10 to surrounding soft tissues in the knee area. Furthermore, it is presently conceived that a meniscus prosthetic device 10 can be constructed without prominences 15, 16, in which case either sutures 17, fibrous tissue ingrowth into a porous border, or a combination thereof, would be utilized to securely position the device.

The cross-sectional area of the exterior portion 40 of the prosthetic device 10 when viewed in FIG. 4, is greater than the cross-sectional area of the interior portion 42. The change in cross-sectional area is gradual. In this manner, the femoral condyle can interact with and rest in the depressed portion formed by the change in cross-sectional area. FIG. 5 is a cross-section of the device showing prominence 16 and shows the increased cross-sectional area thereof relative to the cross-sectional area of FIG. 4.

FIG. 6 depicts the posterior view of a human right knee joint with the medial and lateral meniscus devices 10 and 60, respectively, in proper position. As stated above, for the right knee, the medial meniscus device 10 is generally that depicted by FIGS. 1-3, while the lateral meniscus prosthetic device 60 for the right knee is generally a mirror image thereof. The right knee medial device 10 generally rests between the inner condyle 61 of the right femur bone 62 and the articular cartilage 63 of the tibia bone 64. Similarly, the right knee lateral meniscus prosthetic device 60 is positioned between the outer condyle 65 of the right femur bone 62 and the articular cartilage 63 of the tibia 64. The prominence 16 of the medial device device and the corresponding prominence 16A of the lateral device can be seen in FIG. 6 as superiorly extending into the space 66 defined by the inner and outer condyles 61 and 65, respectively, of the femur bone 62. Optionally, a suture, plurality of sutures, fibrous tissue ingrowth into a porous border, or a combination thereof, may be utilized to further secure the meniscus device to the surrounding soft tissue, such as, for example, the medial collateral ligament, the lateral collateral ligament, or the like.

Referring now more specifically to FIG. 7, wherein a medial view of a human right knee is depicted in extension showing the medial meniscus prosthetic device 10 in proper position, it can be seen that the prosthetic device 10 is positioned between the inner condyle 61 of the femur bone 62 and the articular cartilage 63 of the tibia 64. It should be particularly noted that the femoral condyle articular cartilage 70 and the tibial articular cartilage 63 are intact. An optional suture 17 can be seen in FIG. 7 as being attached to the medial collateral ligament 72 for further securement of the medial meniscus prosthetic device 10 as desired by the attending physician.

Referring to FIG. 8, wherein a medial view of a human right knee during flexion is depicted, it can be seen that the medial meniscus prosthetic device 10 is moved posteriorly from position A to position B with the corresponding flexion of the knee. Position A and position B represent the maximum postional movement during flexion. It should, therefore, be understood that the prosthetic device can translate to any position therebetween and, additionally, slightly rotate according to the natural movement of the knee.

The prosthetic device of the present invention may be constructed from an elastic, self-supporting material, such as, for example, silicone rubber. The prosthetic device 10 can, thus, be elastically deformed, and recover from such structural deformation readily. Therefore, in a method of inserting a meniscus prosthetic device of the present invention, and again referring to the representative medial meniscus prosthetic device 10 of FIG. 1, opposing forces may be applied to the terminal ends 11, 12 of the prosthetic device 10 enlarging the corresponding space 13 defined between the terminal ends 11, 12. With the force thus applied, the attending physician can then insert the meniscus device between the femoral condyle and the tibial articular cartilage. When the prosthetic device 10 is properly in place, the opposing forces previously applied can be released causing the prominences 15 16 to enter the space defined by the femoral condyles. The prominences 15, 16 secure the device while, simultaneously, encouraging rotary and anterior-posterior translation of the device during knee flexion. Once again, it should be understood that the method of inserting the medial meniscus device of the right knee discussed above is also representative of the lateral device of the right knee and, in addition, is representative of the method utilized for inserting the medial and lateral devices for the left knee.

Thus, it can be seen that according to the present invention a meniscus prosthetic device and method of inserting same has been provided that prevent and reverse degenerative changes in the knee joint. The meniscus prosthetic device of the present invention can be easily manufactured and inserted in a patient's knee without the necessity of removing or altering the femoral articular cartilage of the condyles or the tibial articular cartilage. Furthermore, the meniscus device of the present invention freely translates over the articulating surfaces of the tibia and does not have to firmly attached thereto.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A meniscus prosthetic device to prevent and reverse degenerative changes in a human knee comprising:

means for replacing natural components of a condylar joint so that the articular cartilage therein remains intact, and comprising a body including means for encouraging rotary and anterior-posterior translation of said prosthetic device when in direct communication with the condyle joint of a human knee during motion; and means for providing elastic deformation of said body to conform to changing condylar profiles of a human knee during motion.

2. A meniscus prosthetic device to prevent and reverse degenerative changes in a human knee comprising:
   a flexible generally C-shaped structure for replacing natural components of a condylar joint in a human knee, said structure defining a generally interior circular space, and constructed from an elastic, self-supporting material compatable with human tissue and capable of recovering from structural deformation, and having anterior and posterior prominences opposingly disposed at each of the terminal ends of said structure, said prominences being adapted to superior extension into the space defined by the femoral condyles of a human knee and having a greater cross-sectional area at the exterior portion of said structure relative to the corresponding interior portion thereof.

3. A meniscus prosthetic device as recited in claims 1 or 2 wherein said device is a lateral prosthesis sized to fit the outer condyle joint in a human knee.

4. A meniscus prosthetic device as recited in claims 1 or 2 wherein said device is a medial prosthesis sized to fit the inner condyle joint in a human knee.

5. A meniscus prosthetic device as recited in claim 1 wherein said body has terminal ends, and wherein said means for encouraging rotary and anterior-posterior translation are anterior and posterior prominences opposingly disposed at each of the terminal ends of said body, said prominences constructed to extend into the space defined by the femoral condyles of a human knee.

6. A meniscus prosthetic device as recited in claim 1 wherein said means for providing elastic deformation of said body is an elastic, self-supporting material capable of recovering from structural deformation, said body consisting essentially of said material.

7. A meniscus prosthetic device as recited in claims 2 or 6 wherein said elastic, self-supporting material is silicone rubber.

8. A meniscus prosthetic device as recited in claim 1 further comprising means for securing said body to surrounding soft tissue.

9. A meniscus prosthetic device as recited in claim 8 wherein said means for securing said body is at least one suture.

10. A meniscus prosthetic device as recited in claim 8 wherein said means for securing said body is fibrous tissue ingrowth into a porous border.

11. A meniscus prosthetic device as recited in claim 8 wherein said means for securing said body comprises:
   at least one suture; and
   fibrous tissue ingrowth into a porous border.

12. A device as recited in claim 2 wherein the transition in cross-section from said exterior portion to said interior portion is gradual.

13. A method of inserting in a human knee without removal or alteration of the articular cartilage therein a meniscus prosthetic device comprising, a C-shaped structure formed of biocompatible, flexible and resilient material, and having terminal ends defining a space therebetween, the method comprising the steps of:
   (a) applying opposing forces upon the terminal ends of the device so that the device is deformed and the space defined between the terminal ends is enlarged;
   (b) positioning the device deformed according to step (a) between one femoral condyle and the corresponding tibial articular cartilage; and
   (c) releasing the opposing forces applied in step (a) so that the device is held in place between one femoral condyle and the corresponding tibial articular cartilage.

14. A method as recited in claim 13 wherein the device includes a pair of prominences formed on the terminal ends of the C-shaped structure extending out of the plane of the C-shaped structure, and wherein step (b) and (c) are practiced to position the prominences of the device superiorly extending into the space defined by the femoral condyles.

15. A method as recited in claim 14 or 14 further comprising the step of:
   (d) securing the device with at least one suture.

16. A method as recited in claims 13 and 14 further comprising the step of:
   (d) securing the device with fibrous tissue ingrowth into a porous border.

17. A method as recited in claim 15 further comprising the step of:
   (e) securing the device with fibrous tissue ingrowth into a porous border.

* * * * *